(12) United States Patent
Hahn et al.

(10) Patent No.: US 11,096,740 B2
(45) Date of Patent: Aug. 24, 2021

(54) ELECTRODE ARRANGEMENT FOR A BIPOLAR RESECTOSCOPE, AND RESECTOSCOPE

(71) Applicant: KARL STORZ SE & Co. KG, Tuttlingen (DE)

(72) Inventors: Martin Hahn, Leibertingen-Altheim (DE); Rainer Hermle, Gosheim (DE); Franziska Wirth, Villingen-Schwenningen (DE); Uwe Wittke, Bad Dürrheim (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 154 days.

(21) Appl. No.: 16/675,514

(22) Filed: Nov. 6, 2019

(65) Prior Publication Data

US 2020/0146746 A1    May 14, 2020

(30) Foreign Application Priority Data

Nov. 8, 2018  (DE) .................... 10 2018 127 919.1

(51) Int. Cl.
*A61B 18/14*    (2006.01)
*A61B 17/00*    (2006.01)
*A61B 18/00*    (2006.01)

(52) U.S. Cl.
CPC .... *A61B 18/149* (2013.01); *A61B 2017/0088* (2013.01); *A61B 2018/00148* (2013.01);
(Continued)

(58) Field of Classification Search
CPC ... A61B 18/1482; A61B 18/149; A61B 18/16; A61B 2017/0088; A61B 2018/00077;
(Continued)

(56) References Cited

U.S. PATENT DOCUMENTS 4,116,198 A * 9/1978 Roos ............... A61B 18/12
606/46
5,047,027 A   9/1991 Rydell
(Continued)

FOREIGN PATENT DOCUMENTS

DE       2521719 A1   11/1976
DE   102013001156 A1    7/2014
(Continued)

OTHER PUBLICATIONS

German Search Report (Including Translation) for corresponding German Application No. 10 2018 127 919.1, dated Jul. 29, 2019.
(Continued)

*Primary Examiner* — Michael F Peffley
(74) *Attorney, Agent, or Firm* — Jason H. Vick; Sheridan Ross, PC

(57) ABSTRACT

An electrode arrangement according to the invention for a bipolar resectoscope (50) comprises an elongate electrode carrier (2), an active electrode disposed at a distal end of the electrode carrier (2) and a neutral electrode, wherein a distal end section of the electrode carrier (2) is embodied as an electrode body (4, 40) through which a supply line (20) of the active electrode is guided and wherein the neutral electrode is formed by the electrode body (4, 40) or a portion of the electrode body (4, 40). The invention also relates to a resectoscope (50).

25 Claims, 5 Drawing Sheets

(52) U.S. Cl.
CPC ........... *A61B 2018/00517* (2013.01); *A61B 2018/00559* (2013.01); *A61B 2018/1407* (2013.01); *A61B 2018/1417* (2013.01)

(58) Field of Classification Search
CPC .......... A61B 2018/00083; A61B 2018/00148; A61B 2018/00517; A61B 2018/00559; A61B 2018/00577; A61B 2018/00601; A61B 2018/00625; A61B 2018/00982; A61B 2018/1407; A61B 2018/1417; A61B 2018/144; A61B 2018/162
See application file for complete search history.

(56) References Cited

U.S. PATENT DOCUMENTS

| | | | |
|---|---|---|---|
| 6,471,701 | B2 | 10/2002 | Brommersma et al. |
| 6,575,968 | B1 * | 6/2003 | Eggers ................ A61B 18/148 606/41 |
| 7,429,262 | B2 * | 9/2008 | Woloszko ......... A61M 25/0133 606/46 |
| 7,611,511 | B2 | 11/2009 | Blocher |
| 2001/0053908 | A1 | 12/2001 | Brommersma et al. |
| 2003/0233089 | A1 * | 12/2003 | Ohyama ............... A61B 18/149 606/46 |
| 2015/0066018 | A1 | 3/2015 | Doll et al. |
| 2015/0351826 | A1 * | 12/2015 | Kroeber ............... A61B 18/149 600/105 |
| 2017/0181792 | A1 | 6/2017 | Lin |

FOREIGN PATENT DOCUMENTS

| | | |
|---|---|---|
| DE | 102013109505 A1 | 3/2015 |
| DE | 212016000007 U1 | 1/2017 |
| EP | 1163886 A2 | 12/2001 |
| EP | 1567079 B1 | 8/2006 |

OTHER PUBLICATIONS

European Search Report for corresponding European Application No. 19202505.4, dated Feb. 11, 2020.
Intent to Grant (Including Translation) for corresponding European Application No. 19202505.4, dated Apr. 1, 2020.
German Search Report for corresponding German Application No. 10 2018 127 919.1, dated Jul. 29, 2019.

* cited by examiner

ELECTRODE ARRANGEMENT FOR A BIPOLAR RESECTOSCOPE, AND RESECTOSCOPE

CROSS REFERENCE TO RELATED APPLICATIONS

This application claims the benefit under 35 U.S.C. 119(a) to German Patent Application No. 10 2018 127 919.1, filed Nov. 8, 2018, the disclosure of which is incorporated herein by reference in its entirety.

The present invention relates to an electrode arrangement for a bipolar resectoscope, comprising an elongate electrode carrier, an active electrode disposed at a distal end of the electrode carrier and a neutral electrode. Further, the invention relates to a resectoscope comprising a corresponding electrode arrangement.

Electrode arrangements of the aforementioned type and corresponding resectoscopes are known, in particular for urological and gynecological applications. Here, the electrode arrangement is inserted in longitudinally displaceable fashion into a working element of the resectoscope and connected to an RF generator on the proximal side. Together with the electrode arrangement, the working element is inserted into the body of a patient as far as an operating region, for example through the urethra. RF voltage is applied to the active electrode of the electrode arrangement and said electrode is guided through a tissue region under endoscopic vision. As a result thereof, tissue can be ablated and can be guided away by means of a rinsing liquid. In the case of bipolar resectoscopes, both the active electrode and the neutral electrode are inserted to the operating region. This is advantageous in that the current flow can be restricted to the region between the active electrode and the neutral electrode.

EP 1 567 079 B1 has disclosed a bipolar medical instrument for cutting tissue, comprising an elongate electrode carrier, an active electrode that is disposed on the distal side at the electrode carrier and embodied as a wire loop, and a neutral electrode disposed adjacently on the distal side of the active electrode. The neutral electrode and the active electrode are spaced apart from one another transversely to the longitudinal direction of the electrode carrier.

According to DE 10 2013 001 156 A1, a bipolar resectoscope comprises an inner shaft with an insulation insert arranged at the distal end thereof, an electrode transporter disposable in the inner shaft, a first electrode that is longitudinally displaceable in the electrode transporter and a second electrode. At its distal end, the insulation insert has a circumferential and electrically conductive electrode face that is exposed transversely to the longitudinal axis of the inner shaft, said electrode face being connected at the inner side with the distal end of the second electrode.

A bipolar medical instrument for cutting tissue is disclosed in DE 10 2013 109 505 A1, wherein an active electrode and, adjacent thereto, a neutral electrode are disposed at a distal end and wherein the neutral electrode has a curved profile with a first and a second curve, the respective directions of the curves being different. Here, a mean cross section and/or an extent of the neutral electrode can be greater than in the case of the active electrode.

According to DE 21 2016 000 007 U1, a bipolar electrode with a left and a right parallel loop comprises, inter alia, a positive electrode, two ceramic insulation tubes, a metal sleeve, a rigid tube, two insulation tubes and two lines. A ceramic insulation tube is fastened at the front ends of the metal sleeve and the rigid tube in each case, wherein an end of the positive electrode is connected to one line by way of a ceramic insulation tube in the rigid tube and the other end is supported in the ceramic insulation tube associated with the metal sleeve. The other line is welded onto the associated metal sleeve. Here, the rigid tube does not serve as a loop electrode.

In the known electrode arrangements for bipolar resectoscopes, the neutral electrode requires additional space and/or causes a reduction in the mechanical stability of the electrode arrangement. Further, as a rule, the neutral electrode represents an additional component, as a result of which additional manufacturing and assembly outlay arises.

It is an object of the present invention to specify an improved electrode arrangement for a bipolar resectoscope, wherein the aforementioned disadvantages are avoided to the greatest possible extent, in particular wherein the additional space required by the neutral electrode and/or the manufacturing and assembly outlay are reduced. Further, it is the object of the invention to specify a corresponding resectoscope.

This object is achieved by an electrode arrangement and by a resectoscope as described herein.

Advantageous developments of the invention emerge from the various aspects disclosed herein.

An electrode arrangement according to the invention is embodied for use in a bipolar resectoscope, in particular for urological or gynecological applications. The electrode arrangement comprises an elongate electrode carrier, an active electrode and a neutral electrode, wherein the active electrode is disposed at a distal end of the electrode carrier. The neutral electrode is likewise disposed in the distal end region of the electrode carrier. The electrode carrier is embodied to be received in a shaft of the resectoscope and to be displaced in the longitudinal direction of the shaft by means of a displacement mechanism. The electrode carrier comprises supply lines for the active electrode and for the neutral electrode; typically, the supply lines are guided to a proximal end of the electrode carrier and end there in plug-in connectors, which serve for the electrical connection to an RF connector of the resectoscope. By way of example, the active electrode can be embodied as a wire loop, or else in any other form, and it preferably protrudes beyond the electrode carrier in the distal and/or lateral direction. Such an electrode arrangement is often also referred to in abbreviated fashion as "electrode".

According to the invention, a distal end portion of the electrode carrier is embodied as an electrode body, which can have an integral embodiment, in particular. A supply line of the active electrode is guided through the electrode body; in particular, the supply line of the active electrode extends from a proximal side of the electrode body through the latter to a distal side of the electrode body, which may be formed by a distal end face of the electrode body, for example. The electrode body can be embodied as a hollow body or else it may have a solid embodiment apart from optionally present bores, for instance for supply lines.

According to the invention, the neutral electrode is formed by the electrode body or by a part or portion of the electrode body, in particular by such a part or portion of the electrode body that forms an outer surface of the electrode body or a portion of an outer surface. At least the part or portion of the electrode body that serves as neutral electrode has an electrically conductive embodiment to this end and it is electrically connected to a supply line of the neutral electrode. The neutral electrode can be disposed completely or predominantly on the proximal side of the active electrode. Further, the effective surface of the neutral electrode is preferably larger than a surface of the active electrode.

The electrode arrangement may comprise further elements, for instance guide clamps, for guiding the electrode carrier within a shaft of the resectoscope, or plug-in connectors disposed at the proximal end of the electrode carrier, for connecting the supply lines to corresponding contacts and/or for locking the electrode arrangement in the displacement mechanism of the resectoscope.

During the application of the electrode arrangement, RF voltage is applied to the electrodes. In the process, there is a current flow between the active electrode and the neutral electrode, and so electrosurgical ablation or separation of tissue and possibly a coagulation can be implemented by way of the active electrode. To this end, the active electrode can be displaced together with the neutral electrode by way of a longitudinal displacement of the electrode carrier.

As a result of the distal end section of the electrode carrier being formed by an electrode body, which itself or at least a part of which represents the neutral electrode, it is possible to create a neutral electrode that requires no additional space or only minimal additional space. In particular, a particularly space-saving arrangement can be created by virtue of the supply line of the active electrode being guided through the electrode body, with the neutral electrode simultaneously having a particularly large effective surface. As a further advantage, the active electrode to passive or neutral electrode distance can be increased. As a result thereof, it may be possible to, firstly, achieve an expedient use of the space within the shaft of a resectoscope, with a large lumen being available for further channels and for an endoscope optical unit, and, secondly, facilitate safe cutting, with the tissue only being cut upon contact with the active electrode. Further, this allows the passive or neutral electrode to be no longer situated in the visual field and hence this allows the visual field to be improved. Moreover, as a result of the embodiment of the neutral electrode according to the invention, the latter can be embodied as a compact component which ensures increased stability. Finally, this can simplify the assembly of the electrode arrangement since the neutral electrode does not constitute a separate component but can be assembled together with the electrode body.

According to a preferred embodiment of the invention, the electrode carrier comprises an elongate electrode shaft, the length of which may approximately correspond to a length of a resectoscope shaft, and the distal end section of the electrode carrier or the electrode body is disposed in a distal continuation of the electrode shaft, wherein a cross section of the electrode body in respect of form and size at least approximately corresponds to a cross section of the electrode shaft. This may render an optimal exploitation of the spatial conditions within the shaft of the resectoscope achievable.

Preferably, the electrode shaft and the electrode body are offset from one another and separated from one another by an interstice. Preferably, the electrode shaft and the electrode body are connected to one another by the supply line of the active electrode and the supply line of the neutral electrode, in particular only by the specified supply lines, wherein the supply lines can each be surrounded by an insulating sleeve, at least in the interstice between the electrode body and the electrode shaft. As a result thereof, a surface of the electrode shaft can be insulated from the supply lines and from the neutral electrode at the same time. The connection sections of the supply lines, which lie in the interstice, can have an embodiment with the same length or with different lengths. As a result thereof, a particularly simple structure can be achieved.

Particularly preferably, the supply line of the neutral electrode can moreover be inserted into the electrode body on the proximal side. As a result thereof, a simple and compact structure can be obtained, and achieving an electrical connection of the supply line with the neutral electrode can further be facilitated in a particularly simple and reliable manner.

According to a particularly preferred embodiment of the invention, the electrode body is embodied as an insulation body with an electrically conductive layer, wherein the supply line of the active electrode is guided through the insulation body. According to this aspect of the invention, the electrode body is consequently wholly or predominantly formed by an electrically non-conductive material and the effective surface of the neutral electrode is formed by the electrically conductive layer that is applied to at least a portion of a surface of the insulation body. Consequently, the insulation body serves as a main body, on which the electrically conductive layer is applied at least in part. As a result of the distal end portion of the electrode carrier being formed by an insulation body through which the supply line of the active electrode extends and on the surface of which the neutral electrode is formed by an electrically conductive layer, the active electrode being electrically insulated from the neutral electrode can be brought about in a simple manner. Further, the insulation body with the conductive layer can be embodied as a compact component that is easy to produce and easy to assemble and that ensures particularly high stability.

Preferably, the insulation body consists wholly or predominantly of a ceramic material, or else, optionally, of a different RF-resistant and temperature-resistant material. This has the particular advantage of not only ensuring a reliable insulation of the supply line of the active electrode guided through the insulation body but also having a high mechanical, thermal and chemical stability. Such a ceramic insulation body can be produced in a simple and cost-effective manner in a suitable form, for example as a hollow body or else as a solid body with bores.

Preferably, the electrically conductive layer is an electrically conductive coating, more particularly a metallic coating. The latter can be applied to the surface of the insulation body, for instance as a thin layer, using a conventional coating method. As a result thereof, both a particularly simple production and a particularly stable embodiment of the electrode arrangement are facilitated. Alternatively, the electrically conductive layer can be a thick layer which, for example, can be formed by a component that is applied to the surface of the insulation body and adapted to the form of the surface, for instance a cladding.

Preferably, the portion of the surface of the insulation body on which the electrically conductive layer or the coating forming the effective surface of the neutral electrode is applied is such a portion that represents a lateral surface, more particularly a circumferential surface of the insulation body or of a portion of same. Consequently, the effective surface of the neutral electrode preferably is a lateral surface of the electrode body. Here, the lateral surface refers to a surface that is laterally arranged with respect to a longitudinal axis of the electrode carrier or of the electrode body, in particular such a surface whose surface normal is directed transversely to the longitudinal axis. As a result thereof, a simple structure and cost-effective production as well as reliable insulation and a current distribution that is expedient for the application can be achievable.

Advantageously, the insulation body can be formed at least approximately as a cylinder or a flattened cylinder, wherein at least one portion of the lateral surface of the cylinder is covered as a neutral electrode and covered with the electrically conductive layer or the coating to this end. The flattened cylinder and the layer applied to the surface can be embodied, at least in sections, in mirror-symmetric fashion with respect to a longitudinal central plane or in axisymmetric fashion with respect to the longitudinal central axis of the electrode carrier. As a result thereof, a particularly simple design that is also expedient for the application is achieved.

According to an advantageous embodiment of the invention, a supply line of the neutral electrode is inserted on the proximal side into the insulation body and the insulation body has a transverse bore which reaches as far as the supply line of the neutral electrode inserted into the insulation body and in which transverse bore the layer or the electronically conductive, more particularly metallic coating extends as far as the surface of the supply line. As a result thereof, the electrical contact between the layer or the electronically conductive, more particularly metallic coating forming the neutral electrode and the supply line can be established in a particularly simple fashion.

Particularly preferably, the active electrode is embodied as a cutting loop with a first and a second base section and a cutting section lying therebetween, wherein the first and the second base section are each positioned at a distal end face of the insulation body, said end face in particular not containing the electrically conductive layer. The first base section is connected to the supply line of the active electrode in this case, or has a continuous embodiment with the latter, while the second base section is inserted into the insulation body without an electrical connection to a supply line. Consequently, the active electrode is only electrically connected to the supply line via its first base section while the second base section is supported by the insulation body but separated thereby from the neutral electrode and the supply line thereof. As a result of this, a particularly simple, stable and easily manageable active electrode can be developed.

Alternatively, the active electrode can have a rod-shaped embodiment with only a single base section, for example, said base section being positioned at the distal end face of the insulation body and being connected with, or merging into, the supply line of the active electrode, wherein the rod is preferably directed transversely to the longitudinal axis of the electrode body or of the electrode shaft. Additionally, the active electrode can comprise a metallic sphere or any other element with a suitable electrode surface at the end of the rod distant from the base section. An electrode arrangement with such an embodiment is likewise simple and stable and, for example, suitable for cutting and/or coagulating tissue.

According to a further preferred embodiment of the invention, the distal end section of the electrode carrier is embodied as a metallic electrode body, which forms the neutral electrode and through which the supply line of the active electrode is guided in insulated fashion. In particular, the supply line of the active electrode is guided in insulated fashion through the metallic electrode body from a proximal side to a distal side thereof and, to this end, said supply line is surrounded by an insulating sleeve, for example. The insulating sleeve can extend beyond the metallic electrode body in the proximal and/or the distal direction. By way of example, the metallic electrode body can have an embodiment approximately in the form of a cylinder or a flattened cylinder. Such a metallic electrode body, too, can be produced in a simple and cost-effective manner in a suitable form, for example as a hollow body or else as a solid body with bores. As a result thereof, a particularly simple, space-saving and stable electrode arrangement can likewise be created.

Advantageously, the active electrode can be embodied as a cutting loop with a first and a second base section and a cutting section lying therebetween, wherein the first and the second base section are positioned at a distal end of the supply line of the active electrode. In particular, an insulating sleeve, which surrounds the supply line of the active electrode within the metallic electrode body and which electrically insulates the active electrode from the neutral electrode, can project beyond a distal end face of the metallic electrode body on the distal side, wherein at least the first base section is connected to, or merges into, the supply line in electrical fashion in the distal end region of the insulating sleeve and said first base section is mechanically supported thereby at the same time. As a result thereof, a simple, effective and easily manageable electrode arrangement can be created.

Alternatively, the active electrode can have a rod-shaped embodiment and can be embodied with only a single base section, which is connected to the supply line of the active electrode in the distal end region of the insulating sleeve. Otherwise, the active electrode according to this embodiment can be embodied like the rod-shaped electrode described above and, for example, can additionally carry a metallic sphere or any other element with a suitable electrode surface at the end of the rod distant from the base section.

A resectoscope according to the invention comprises an elongate shaft, an electrode arrangement embodied according to the invention that is inserted in said shaft in longitudinally displaceable fashion and a displacement mechanism for displacing the electrode arrangement in the longitudinal direction of the shaft. Further, the shaft can be embodied to receive an endoscope optical unit. The shaft with the displacement mechanism is usually also referred to as "working element" and the assembly of the working element and the inserted electrode arrangement is usually, and in the present application, referred to as a "resectoscope"; sometimes, the term "resectoscope" is also used for the working element on its own or for the assembly of working element, electrode and endoscope optical unit.

The shaft of the resectoscope is dimensioned, in particular, for insertion into a body orifice of a human or animal body, for example for insertion into the urethra of a human, and can comprise an outer shaft embodied as an elongate hollow tube and an inner shaft inserted in the latter and connected to the outer shaft by way of a coupling mechanism. Typically, a handle is disposed at the proximal end of the inner shaft, said handle comprising the displacement mechanism for the axial displacement of the electrode arrangement inserted into the inner shaft. At the proximal end region of the shaft or at the handle, provision can furthermore be made of a rinsing connection, a suction connection and one or more electrical connections and an optical coupling for securing the endoscope optical unit inserted into the shaft.

At its proximal end, the electrode carrier of the electrode arrangement may have plug-in connectors, by means of which the active and the neutral electrode are contactable with an RF connector of the resectoscope in order to connect the supply lines of the active electrode and the neutral electrode to an external RF generator that generates the RF voltage required. Further, the electrode carrier can be lockable in the displacement mechanism in order to facilitate a controllable longitudinal displacement.

It is understood that the features specified above and the features yet to explained below are usable not only in the respectively specified combination but also in other combinations or on their own, without departing from the scope of the present invention.

Further aspects of the invention emerge from the following description of preferred exemplary embodiments and from the attached drawing. In detail:

Figure 1:
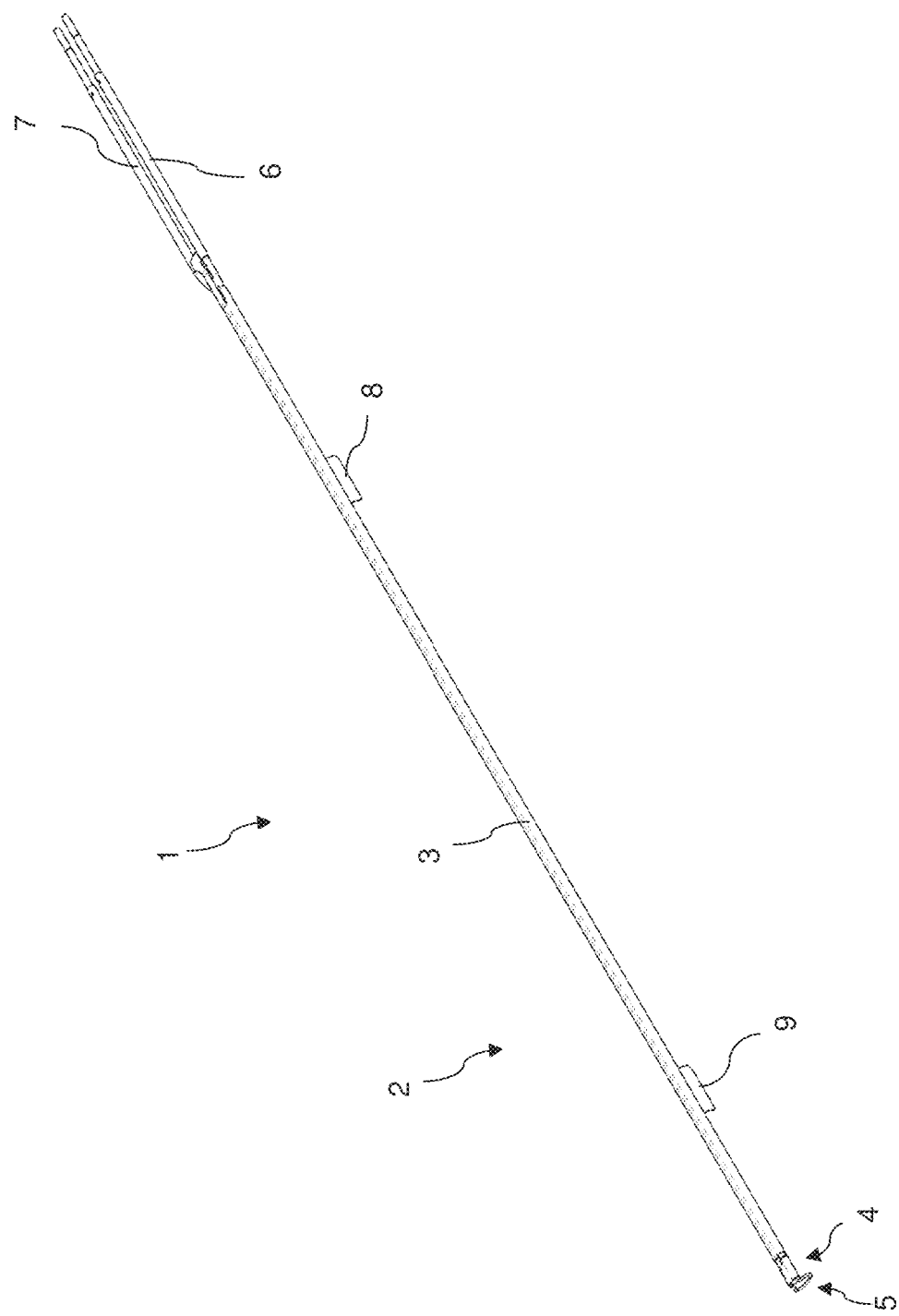
FIG. 1 shows an electrode arrangement according to a first exemplary embodiment of the invention in an overall view.

FIG. 1 shows, in exemplary fashion, an electrode arrangement according to a first exemplary embodiment of the invention in an overall view. The electrode arrangement 1 comprises an electrode carrier 2, which has an elongate electrode shaft 3 and an electrode body 4 arranged at the distal end of the latter. On the distal side, an active electrode embodied as a cutting loop 5 is positioned at the electrode body 4. On the proximal side, two parallel plug-in connectors 6, 7 are provided at the electrode shaft 3, said plug-in connectors serving to establish an electrical connection with corresponding electrical contacts of the working element of a resectoscope and also being able to be configured for mechanical locking in the displacement mechanism of the resectoscope. Guiding clamps 8, 9 for guidance within a shaft of the working element of the resectoscope (see FIG. 7) are attached to the electrode shaft 3.

Figure 2:
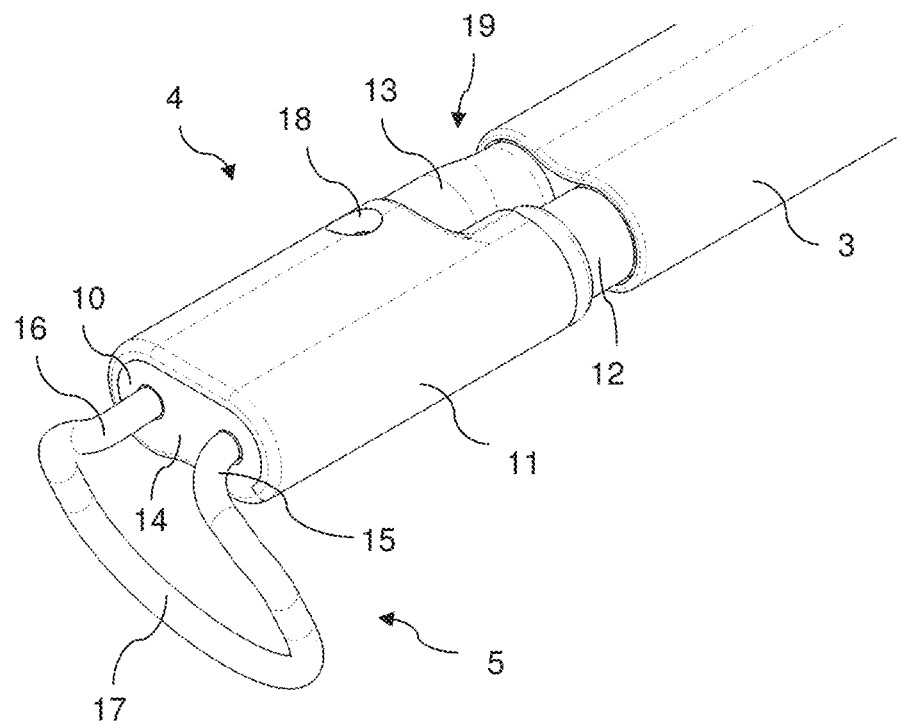
FIG. 2 shows the distal end region of the electrode arrangement of FIG. 1 in an oblique view.

FIG. 2 shows the distal end region of the electrode arrangement 2 in a magnified view, obliquely from the distal direction. The electrode body 4 is disposed at the distal end of the electrode shaft 3 in a straight continuation of the electrode shaft 3. Said electrode body has approximately the same cross section as the electrode shaft 3. In the illustrated exemplary embodiment, the electrode shaft 3 and the distal end section each approximately have the form of a flattened cylinder.

The electrode body 4 is formed by a ceramic insulation body 10, the surface of which is partly covered by an electronically conductive, more particularly metallic coating 11. The coating 11 covers the top side of the lateral surface of the approximately flattened-cylinder-shaped insulation body 10 and extends slightly beyond the middle thereof in the downward direction. The coating 11 could have been applied to the corresponding surface regions of the insulation body using conventional coating methods. The end sides of the insulation body 10 are not covered by the coating 11. On the proximal side, the electrode body 4 is connected to the electrode shaft by way of two supply lines, which are each surrounded by an insulating sleeve 12, 13. The active electrode embodied as a cutting loop 5 is positioned at the distal end face 14. In the exemplary embodiment illustrated in FIG. 2, the cutting loop has a first base section 15 and a second base section 16, by means of which it is positioned at the distal end face 14 of the insulation body 10, and a cutting section 17 lying therebetween, which protrudes downward beyond a distal-side continuation of the cross section of the electrode body 4 or of the electrode shaft 3 and which is brought into contact with tissue for the purposes of cutting the latter. The insulation body 10 has a transverse bore 18, into which the coating 11 extends (see below).

Figure 3:
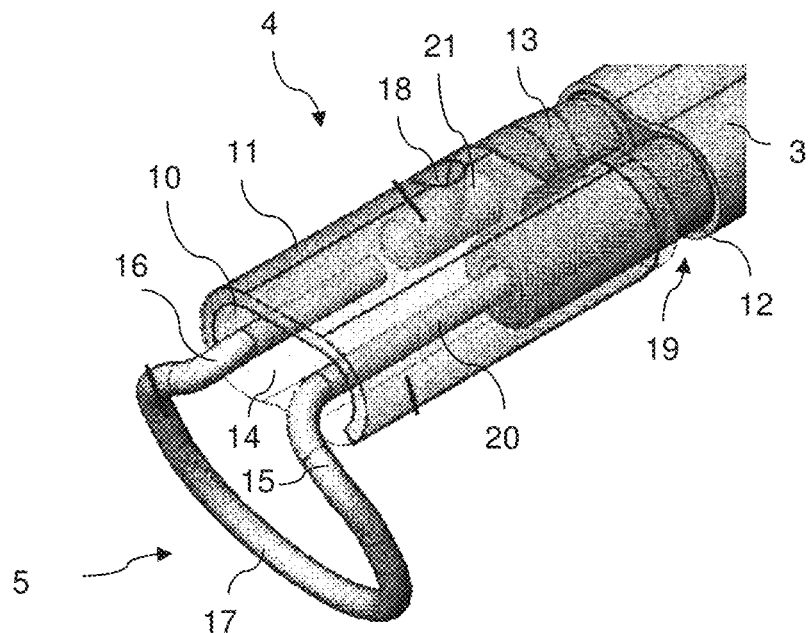
FIG. 3 shows the distal end region of the electrode arrangement of FIG. 1 in a partly transparent representation.

In FIG. 3, the electrode body 4 is shown in a partly transparent representation. As is evident from FIG. 3, the first base section 15 of the cutting loop 5 merges into a supply line 20 within the insulation body 10. The supply line 20 provides the electrical connection of the cutting loop 5 to an RF connector of the resectoscope and is guided through the electrode shaft 3 into the plug-in connector 6 (see FIG. 1). The supply line 20 is surrounded by the insulating sleeve 12 within the electrode shaft and in an interstice 19 between the electrode shaft 3 and the electrode body 4, said insulating sleeve also extending a little into the electrode body 4. The second base section 16 of the cutting loop 5 is inserted into the insulation body 10 but not electrically contacted. The cutting loop 5 can be embodied as a continuous wire with the supply line 20.

A further supply line 21, which provides the electrical connection between the neutral electrode formed by the coating 11 and a corresponding RF connector of the resectoscope via the connection plug 7, extends through the electrode shaft 3 (see FIG. 1). As is evident from FIG. 3, the supply line 21 of the neutral electrode is surrounded by the insulating sleeve 13 in the interstice 19 between the electrode shaft and the distal end portion and said supply line extends slightly into the insulation body 10. The transverse bore 18 reaches up to the surface of the supply line 21. The coating 11 extends into the transverse bore to the supply line 21 and consequently establishes the electrical contact with the supply line 21. As indicated in FIG. 2, the proximal end side of the electrode body 4 has a stepped embodiment, with the supply line 20 of the active electrode bridging the interstice 19 with a shorter section while the supply line 21 of the neutral electrode bridges the interstice with a longer section in order to compensate a transverse offset between the supply lines 20, 21.

The described arrangement establishes, firstly, a supply of the cutting loop 5 with the RF power required for cutting and, secondly, a connection of the coating 11, which represents the effective face of the neutral electrode, to the supply line 21. At the same time, the ceramic material of the insulation body 10, in which the supply lines 20, 21 and the base sections 15, 16 of the cutting loop 5 are embedded, ensures an electrical separation of the active electrode and the neutral electrode. Finally, the insulation body 10 serves to support the cutting loop 5 and serves as a main body for applying the coating 11.

Figure 4:
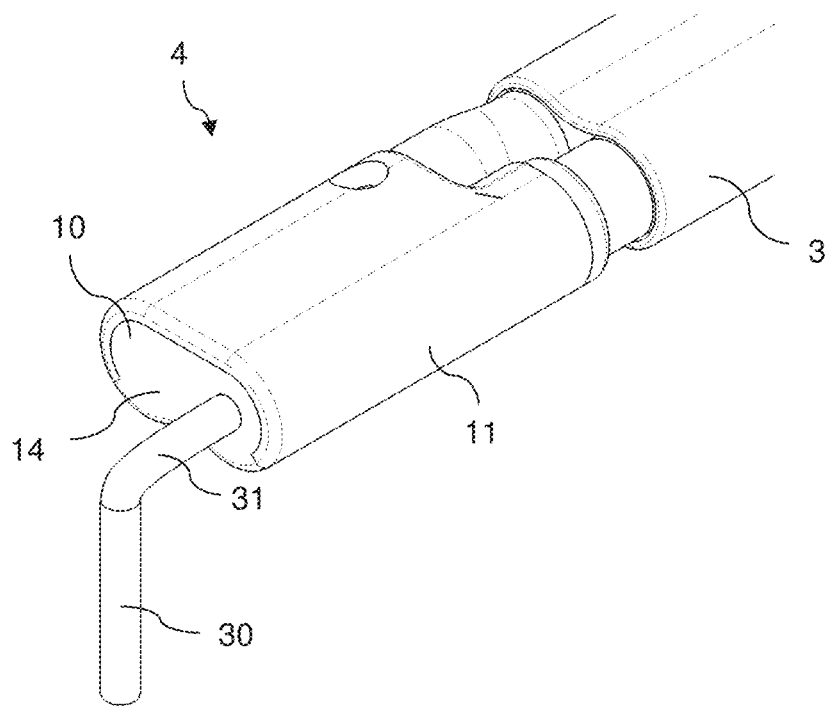
FIG. 4 shows the distal end region of an electrode arrangement according to a second exemplary embodiment of the invention.

FIG. 4, which shows a view corresponding to that of FIG. 2, illustrates the distal end region of the electrode arrangement according to a further exemplary embodiment of the invention. In this exemplary embodiment, the cutting electrode is embodied in the form of a metallic rod 30 that extends transversely to the longitudinal direction of the electrode shaft 3 and of the distal end section 4. The rod 30 is positioned at the distal end face 14 of the insulation body 10 via the base section 31 and is connected to the supply line 20, wherein the rod 30, the base section 31 and the supply line 20 may be formed by a continuous wire. Otherwise, the electrode arrangement according to this exemplary embodiment is embodied like the one described above on the basis of FIGS. 1 to 3.

Figure 5:
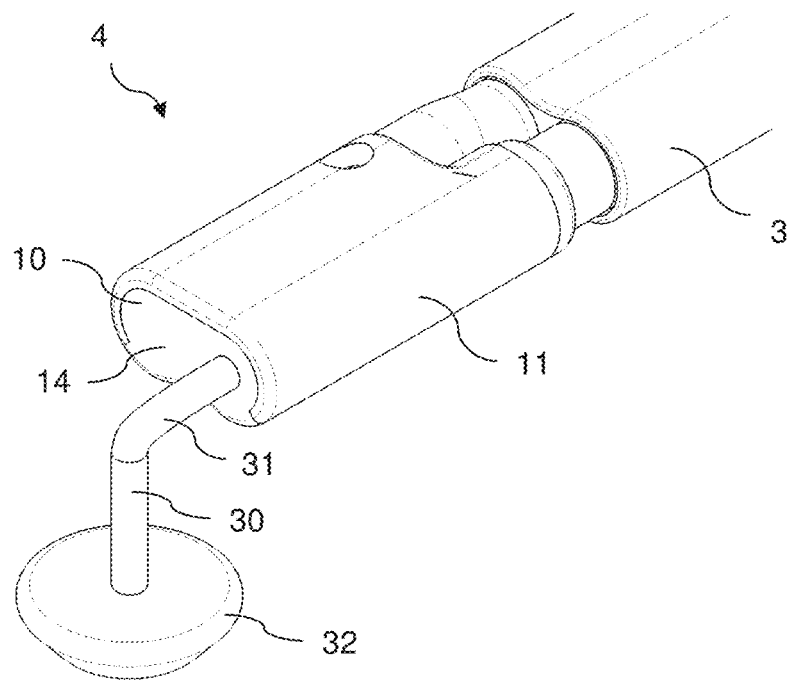
FIG. 5 shows the distal end region of an electrode arrangement according to a third exemplary embodiment of the invention.

A third embodiment of the electrode arrangement according to the invention is shown in FIG. 5. Here, the cutting electrode is embodied like the one shown in FIG. 4 with a rod 30 and a single base section 31, with the rod 30 additionally carrying a metallic sphere 32 at its end distant from the base section 31. Instead of the sphere 32, provision can also be made of a hemisphere or disk, for example. Otherwise, this embodiment is embodied as described above.

Figure 6:
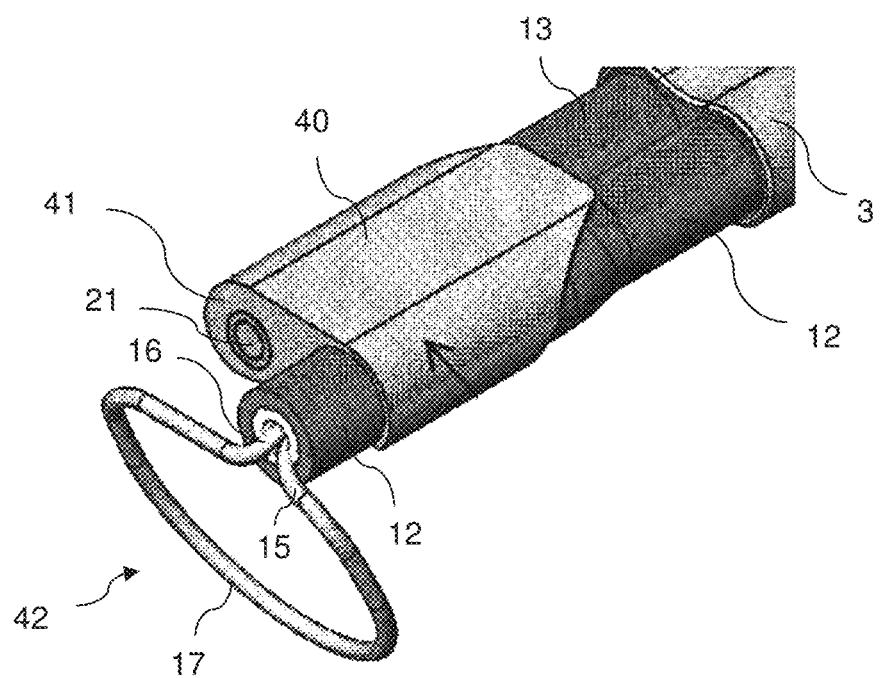
FIG. 6 shows the distal end region of an electrode arrangement according to a fourth exemplary embodiment of the invention.

In the further embodiment of the invention illustrated in FIG. 6, the distal end section of the electrode carrier 2 is not formed by an insulation body 10 provided with an electronically conductive, more particularly metallic coating 11 like in the exemplary embodiments described above, but by a metallic electrode body 40 which represents the neutral electrode at the same time. Together with its insulating sleeve 12, the supply line of the active electrode is guided through the electrode body 40 to beyond the distal end face 41 thereof and said supply line carries at its distal end the active electrode embodied as a cutting loop 42, with both base regions 15, 16 of the cutting loop 42 merging into the insulating sleeve 12 and at least one thereof being electrically connected to the supply line 20. The cutting loop 42 can be formed by the distal end section of a wire that constitutes the supply line 20. The supply line 21 of the neutral electrode is guided within its insulating sleeve 13 into the electrode body 40 and electrically contacted there by the latter. As indicated in FIG. 6, the supply line 21 can extend through the electrode body 40 to the distal end face 41 thereof. Otherwise, the electrode arrangement according to this exemplary embodiment is embodied as described above in relation to FIGS. 1 to 5.

Figure 7:
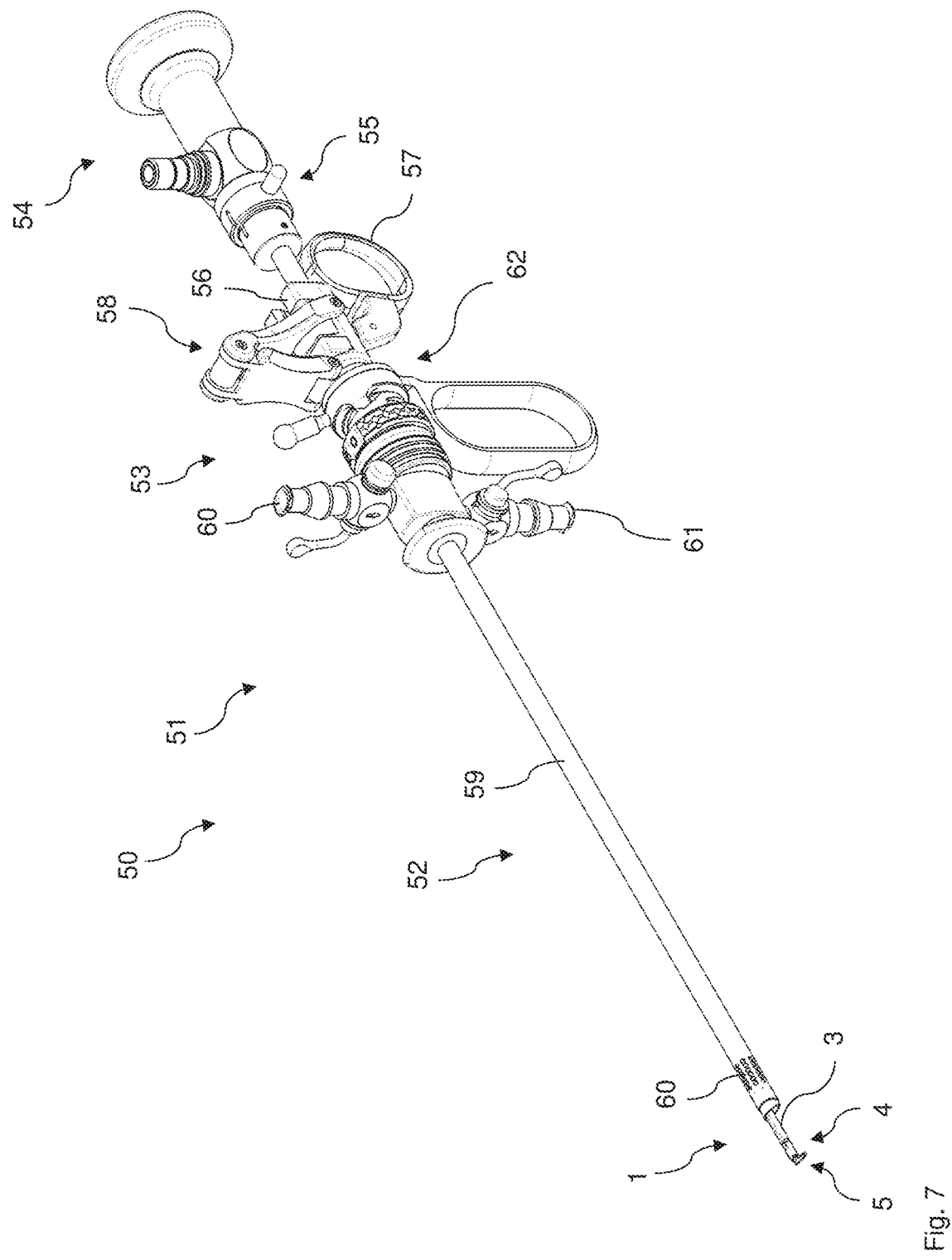
FIG. 7 shows a resectoscope with an electrode arrangement according to FIG. 1.

A resectoscope with an electrode arrangement according to the invention inserted into the former is illustrated in exemplary fashion in an overall view in FIG. 7. The resectoscope 50 comprises a working element 51 with an elongate shaft 52, which is dimensioned for the insertion into a natural or artificial body orifice, and a handle 53, which remains outside of the body of the patient during an application and which comprises connectors, operating elements and a displacement mechanism. As illustrated in FIG. 7, an electrode arrangement 1 is inserted into the shaft 52 of the working element. Further, an endoscope optical unit 54 is inserted into the working element from the proximal direction and said endoscope optical unit is locked with the working element 51 by way of an optics coupling 55.

The electrode arrangement 1 is inserted into the shaft 52 and, further, into the handle 53 of the working element 51 in such a way that said electrode arrangement, on the proximal side, is inserted into a connection block 56 by means of the plug-in connectors 6, 7 (see FIG. 1) and electrically contacted and mechanically locked in said connection block. The connection block 56 is embodied as a displaceable carriage that can be displaced relative to the shaft 52 in the axial direction by means of a gripping ring 57. An RF cable for connection to an external RF current source can be connected to the connection block 56. The connection block 56 is spring-loaded in the proximal direction by way of the lever mechanism 58. The shaft 52 comprises an outer shaft 59 and an inner shaft, only identifiable very distally in FIG. 7, said shafts forming channels for supplying and draining rinsing liquid. To this end, rinsing openings 60 and rinsing connectors 61, 62 are provided. The outer shaft 59 with the rinsing connectors 61, 62 can be connected to the remaining elements of the working element via a coupling 63.

During the application, the shaft 52 with the electrode arrangement 1 inserted therein is inserted into the body of a patient up to an operating region. The connection block 56 with the electrode arrangement 1 is moved in the distal direction counter to the spring force by means of the gripping ring 57 such that the electrode body 4 with the cutting loop 5 projects from the shaft 52 of the resectoscope 50 on the distal side; this position is shown in FIG. 7. For the purposes of cutting tissue, the cutting loop 5 is thereupon pulled through the tissue to be separated by means of the spring force under the application of RF voltage; in its proximal end position, the electrode arrangement 1 is wholly or largely received in the outer shaft 59 (not shown in FIG. 7). Severed tissue parts can be drained by rinsing with a rinsing liquid. Instead of the embodiment of the electrode arrangement 1 illustrated in FIG. 7, use can also be made of any other of the electrode arrangements according to the invention, which are described above in exemplary fashion.

Not all reference signs are illustrated in all figures for reasons of clarity. Reference signs not explained in relation to one figure have a corresponding meaning as in the remaining figures.

LIST OF REFERENCE SIGNS

1 Electrode arrangement
2 Electrode carrier
3 Electrode shaft
4 Electrode body
5 Cutting loop
6 Plug-in connector
7 Plug-in connector
8 Guiding clamp
9 Guiding clamp
10 Insulation body
11 Coating
12 Insulating sleeve
13 Insulating sleeve
14 End face
15 Base section
16 Base section
17 Cutting section
18 Transverse bore
19 Interstice
20 Supply line
21 Supply line
30 Rod
31 Base section
32 Sphere
40 Electrode body
41 End face
42 Cutting loop
50 Resectoscope
51 Working element
52 Shaft
53 Handle
54 Endoscope optical unit
55 Optics coupling
56 Connection block
57 Gripping ring
58 Lever mechanism
59 Outer shaft
60 Rinsing openings, return flow
61 Rinsing connector, supply
62 Rinsing connector, drain
63 Coupling

The invention claimed is:

1. An electrode arrangement for a bipolar resectoscope, comprising an elongate electrode carrier, an active electrode disposed at a distal end of the electrode carrier and a neutral electrode, wherein a distal end section of the electrode carrier is embodied as an electrode body through which a supply line of the active electrode is guided and wherein the neutral electrode is formed by the electrode body or a portion of the electrode body, wherein, the electrode body includes an insulation body with an electrically conductive layer which is applied to at least a portion of an exterior surface of the insulation body, a supply line of the neutral electrode is inserted into the insulation body on a proximal side and the electrically conductive layer extends continuously through a transverse bore of the insulation body to electrically contact the supply line of the neutral electrode within the insulation body, and a cutting section of the active electrode protrudes downward beyond a distal-side continuation of a cross section of the electrode body below the electrode body.

2. The electrode arrangement according to claim 1, wherein the electrode carrier comprises an elongate electrode shaft, wherein the electrode body is disposed in a distal continuation of the electrode shaft and a cross section of the electrode body at least approximately corresponds to a cross section of the electrode shaft.

3. The electrode arrangement according to claim 1, wherein the electrode shaft and the electrode body are connected by the supply line of the active electrode and a supply line of the neutral electrode.

4. The electrode arrangement according to claim 1, wherein the insulation body consists at least predominantly of a ceramic or any other RF-resistant and temperature-resistant material.

5. The electrode arrangement according to claim 1, wherein the electrically conductive layer is an electronically conducting metallic coating.

6. The electrode arrangement according to claim 1, wherein the portion of the surface is a lateral surface or a portion of a lateral surface of the electrode body.

7. The electrode arrangement according to claim 1, wherein the electrode body is embodied at least approximately as a cylinder or a flattened cylinder, wherein the portion of the surface is at least one portion of a lateral surface of the cylinder.

8. The electrode arrangement for a bipolar resectoscope according to claim 1, wherein the electrode body includes a metallic electrode body that forms the neutral electrode and the supply line of the active electrode is guided therethrough in insulated fashion.

9. The electrode arrangement according to claim 8, wherein the active electrode is embodied as a cutting loop with a first and a second base section and a cutting section lying therebetween, wherein the first and the second base section are positioned at a distal end of the supply line of the active electrode.

10. An electrode arrangement for a bipolar resectoscope, comprising an elongate electrode carrier, an active electrode disposed at a distal end of the electrode carrier and a neutral electrode, wherein a distal end section of the electrode carrier is embodied as an electrode body through which a supply line of the active electrode is guided and wherein the neutral electrode is formed by the electrode body or a portion of the electrode body, wherein the electrode body includes an insulation body with an electrically conductive layer which is applied to at least a portion of an exterior surface of the insulation body, and wherein the active electrode is formed as a cutting loop with a first and second base section, and a cutting section lying therebetween, wherein the first and the second base sections are positioned at a distal end face and secured within the insulation body, and only the first base section is connected to the supply line of the active electrode while the second base section terminates within the insulation body and is surrounded thereby.

11. The electrode arrangement according to claim 10, wherein the insulation body consists at least predominantly of a ceramic or any other RF-resistant and temperature-resistant material.

12. The electrode arrangement according to claim 10, wherein the electrically conductive layer is an electronically conducting metallic coating.

13. The electrode arrangement according to claim 10, wherein the portion of the surface is a lateral surface or a portion of a lateral surface of the electrode body.

14. The electrode arrangement according to claim 10, wherein the electrode body is embodied at least approximately as a cylinder or a flattened cylinder, wherein the portion of the surface is at least one portion of a lateral surface of the cylinder.

15. The electrode arrangement according to claim 10, wherein the electrode carrier comprises an elongate electrode shaft, wherein the electrode body is disposed in a distal continuation of the electrode shaft and a cross section of the electrode body at least approximately corresponds to a cross section of the electrode shaft.

16. The electrode arrangement according to claim 10, wherein the electrode shaft and the electrode body are connected by the supply line of the active electrode and a supply line of the neutral electrode.

17. An electrode arrangement for a bipolar resectoscope, comprising an elongate electrode carrier, an active electrode disposed at a distal end of the electrode carrier and a neutral electrode, wherein a distal end section of the electrode carrier is embodied as an electrode body through which a supply line of the active electrode is guided and wherein the neutral electrode is formed by the electrode body or a portion of the electrode body, wherein the electrode body includes an insulation body with an electrically conductive layer which is applied to at least a portion of an exterior surface of the insulation body, and a supply line of the neutral electrode is inserted into the insulation body on a proximal side and the electrically conductive layer extends continuously through a transverse bore of the insulation body to electrically contact the supply line of the neutral electrode within the insulation body, wherein the active electrode is embodied as a rod electrode with a rod and a base section, wherein the base section is inserted into a distal end face of the insulation body and connected to the supply line of the active electrode, and wherein a spherical, hemispherical or disk-shaped element is disposed at the end of the rod distant from the base section.

18. The electrode arrangement according to claim 17, wherein the insulation body consists at least predominantly of a ceramic or any other RF-resistant and temperature-resistant material.

19. The electrode arrangement according to claim 17, wherein the electrically conductive layer is an electronically conducting, in particular metallic coating.

20. The electrode arrangement according to claim 17, wherein the portion of the surface is a lateral surface or a portion of a lateral surface of the electrode body.

21. The electrode arrangement according to claim 17, wherein the electrode body is embodied at least approximately as a cylinder or a flattened cylinder, wherein the portion of the surface is at least one portion of a lateral surface of the cylinder.

22. The electrode arrangement according to claim 17, wherein the electrode carrier comprises an elongate electrode shaft, wherein the electrode body is disposed in a distal continuation of the electrode shaft and a cross section of the electrode body at least approximately corresponds to a cross section of the electrode shaft.

23. The electrode arrangement according to claim 17, wherein the electrode shaft and the electrode body are connected by the supply line of the active electrode and a supply line of the neutral electrode.

24. A resectoscope comprising an elongate shaft, an electrode arrangement inserted in longitudinally displaceable fashion in the latter and a displacement mechanism for displacing the electrode arrangement in the longitudinal direction of the shaft, wherein the electrode arrangement is configured as recited in claim 1.

25. A bipolar resectoscope comprising:
an elongate electrode carrier;
an active electrode disposed at a distal end of the electrode carrier;
a neutral electrode disposed at the distal end of the electrode carrier;
an electrode body disposed at the distal end of the electrode carrier which includes an insulating body;
a supply line for the active electrode disposed within and circumferentially surrounded by the insulating body;
a supply line for the neutral electrode disposed within and circumferentially surrounded by the insulating body,
wherein the insulating body is at least partially surrounded by an electrically conductive layer, the electrically conductive layer extending continuously through a transverse bore of the insulation body to electrically contact the supply line for the neutral electrode; and
an active electrode rod or cutting section extending from the active electrode.

* * * * *